United States Patent [19]

Karapita

[11] 4,445,660
[45] May 1, 1984

[54] ADJUSTABLE SUSPENSION SUPPORT

[76] Inventor: Alexander D. Karapita, 38 Robinter Dr., Willowdale, Ontario, Canada, M2M 3R2

[21] Appl. No.: 366,915

[22] Filed: Apr. 9, 1982

[51] Int. Cl.³ ............................................. B42F 15/00
[52] U.S. Cl. .................................. 248/335; 248/337; 248/412
[58] Field of Search .............. 248/337, 335, 336, 412, 248/410, 409; 403/369, 368

[56] References Cited

U.S. PATENT DOCUMENTS

| | | | |
|---|---|---|---|
| 1,858,595 | 5/1932 | Parker et al. | 248/337 |
| 2,261,505 | 11/1941 | Schlesinger | 248/412 X |
| 2,695,800 | 11/1954 | Soucy | 248/337 X |
| 3,048,360 | 8/1962 | Foley | 248/337 |
| 3,112,103 | 11/1963 | Falkenberg | 248/335 X |
| 4,073,456 | 2/1978 | Karapita et al. | 248/337 |

FOREIGN PATENT DOCUMENTS

| | | | |
|---|---|---|---|
| 1449684 | 7/1966 | France | 248/412 |
| 1010458 | 11/1965 | United Kingdom | 248/412 |

*Primary Examiner*—Ramon S. Britts
*Assistant Examiner*—Sarah A. Lechok

[57] ABSTRACT

An adjustable suspension support having a suspensible vertical cylinder, a coaxial shaft in the cylinder, a brake device on the upper end of the shaft, a grip device carried by the lower end of the shaft with an associated lever, a spacer tube between the brake and the grip, and at least one hanger on the support for holding an object. The brake means has a collar carrying spherical bearings and a plug on the end of the shaft retaining the bearings in the cage. The device is rotatable about its vertical axis and it is adjustable vertically by actuating the lever and exerting an upward force on the grip to release the brake.

10 Claims, 5 Drawing Figures

ADJUSTABLE SUSPENSION SUPPORT

FIELD OF THE INVENTION

This invention relates to an adjustable suspension support.

BACKGROUND OF THE INVENTION

Adjustable suspension supports are used for example in hospitals where a support is suspended from the ceiling to carry plasma bottles for intravenous injections. An example of such a support is shown in U.S. Pat. No. 3,191,904 issued June 29, 1965 to A. D. Karapita. Because of the difficulty in adjusting the support rotationally and upwardly it had previously been proposed to use vacuum means with a suspension support, as disclosed in U.S. Pat. No. 4,073,456 issued Feb. 14, 1978 to A. D. Karapita. Since then an improved support, eliminating the need for a vacuum source, has been disclosed in U.S. Pat. No. 4,374,581 issued Feb. 22, 1983 in the name of A. D. Karapita.

The problem with the device disclosed in U.S. Pat. No. 4,374,581 is that the release of the suspended object could impose a burden of unexpected weight on the operator. Also, the mechanism could be released relatively easily by a patient, which could be especially dangerous in the case of a child.

It is an object of the present invention to provide an improved suspension unit which requires the imposition of an upward force to release it for vertical adjustment.

SUMMARY OF THE INVENTION

In its broadest aspect the invention consists of an adjustable suspension support unit comprising a vertical cylinder and means at the upper end of the cylinder for suspension thereof; a shaft coaxially located in the cylinder; brake means slidable in the cylinder and comprising a cylindrical collar coaxial with the shaft, the collar having a plurality of radial apertures located in a circumferential plane thereof, the upper end of the shaft carrying a plug located within the collar adjacent the apertures, the plug having an inverted frustro-conical side wall, a plurality of spherical bearings one located in each aperture of the collar and retained therein by the plug to bear laterally against the cylinder; grip means carried by the lower end of the shaft and including lever means operable to move the grip means axially downward with respect to the shaft; a spacer tube concentric with the shaft and freely slidable thereon, the lower end of the tube abutting the grip means and the upper end abutting the collar when the lever means is not operated; and means connected with the support to carry an object; whereby on operating the lever means and exerting an upward force on the grip means the plug is raised with respect to the collar and the brake means is thereby released.

BRIEF DESCRIPTION OF THE DRAWINGS

An example embodiment of the invention is shown in the attached drawings in which.

DETAILED DESCRIPTION OF PREFERRED EMBODIMENT

Figures 1, 2:
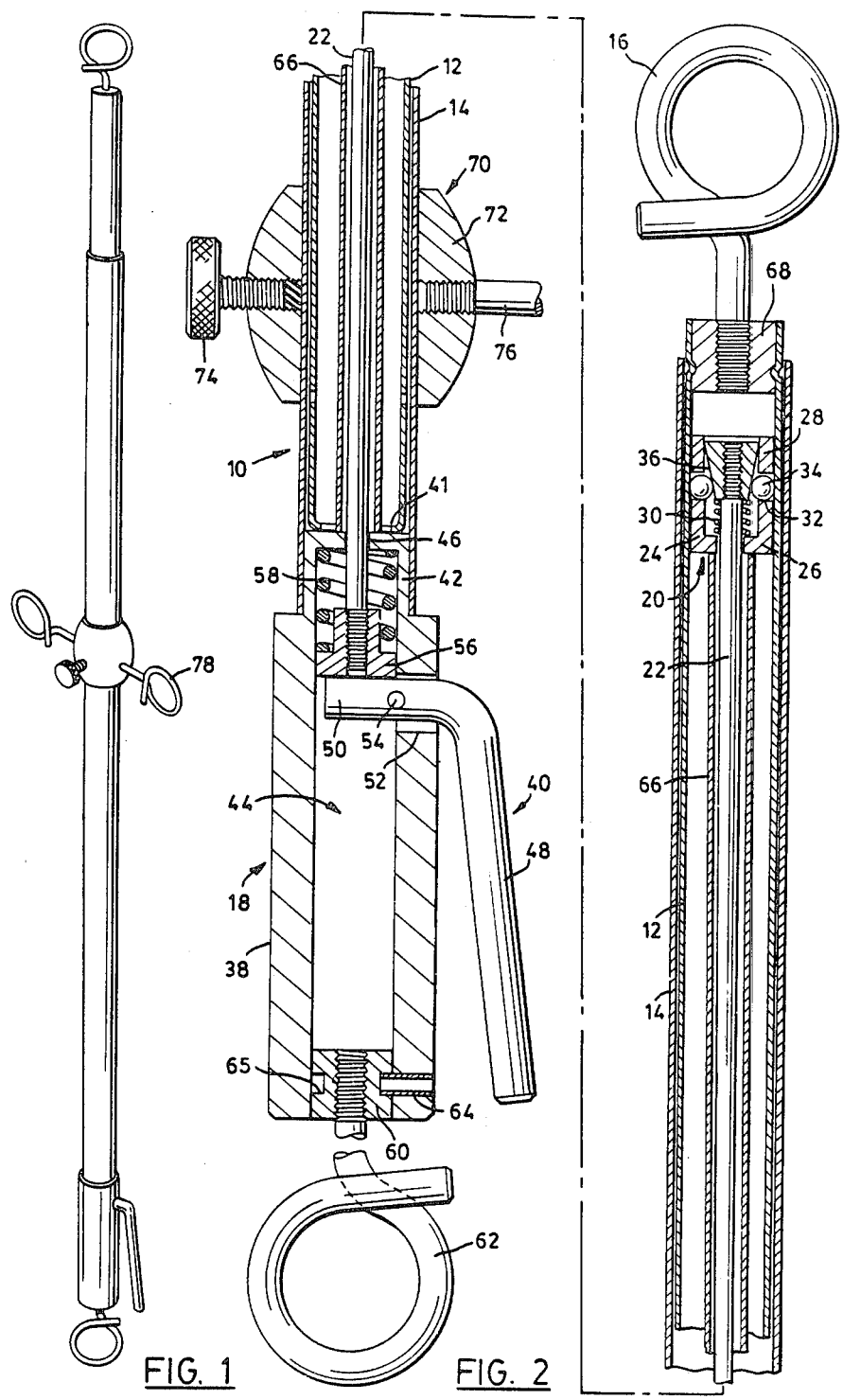
FIG. 1 is a perspective view of a suspension support unit.
FIG. 2 is a vertical cross-sectional view of the support unit of FIG. 1, in a position of rest and fully retracted.

The preferred embodiment consists of a suspension support unit 10 having a pair of vertical telescopic tubes comprising an inner cylinder 12 and an outer sleeve 14 coaxial with the cylinder, an eye hook 16 carried at the top of the cylinder, and a grip 18 connected to the bottom end of the sleeve.

Figure 5:
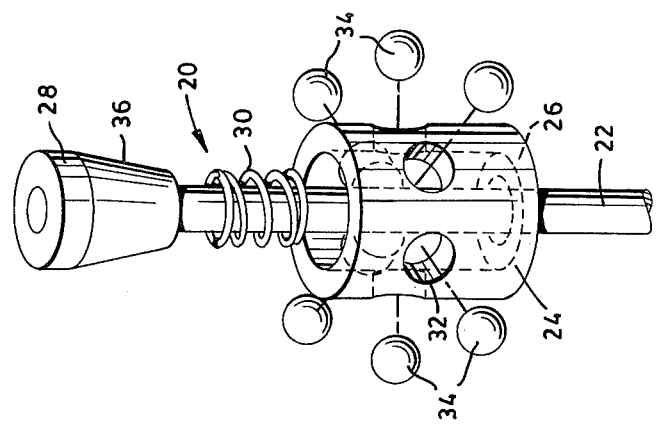
FIG. 5 is an exploded perspective view of the locking mechanism.

A braking mechanism 20 is located slidably within inner cylinder 12 at the upper end of a shaft 22 which is coaxial with the cylinder. Braking mechanism 20 comprises a cage or collar 24 freely slidable along shaft 22 which passes through an inturned circular flange 26 on the lower end of the collar. The top end of shaft 22 is threaded to carry a frustroconical plug 28 which is also vertically slidable in collar 24, separated from flange 26 by a compression spring 30. A ring of equispaced apertures 32 (six in the preferred embodiment as seen in FIG. 5) is located in collar 24 and each aperture receives a spherical bearing 34 freely rotatable within it. Bearings 32 are held in apertures 30 between the inner surface of cylinder 12 and the conical side 36 of plug 28. The preferred slope of side 36 is 15 degrees with respect to the axis of plug 28.

Figure 3:
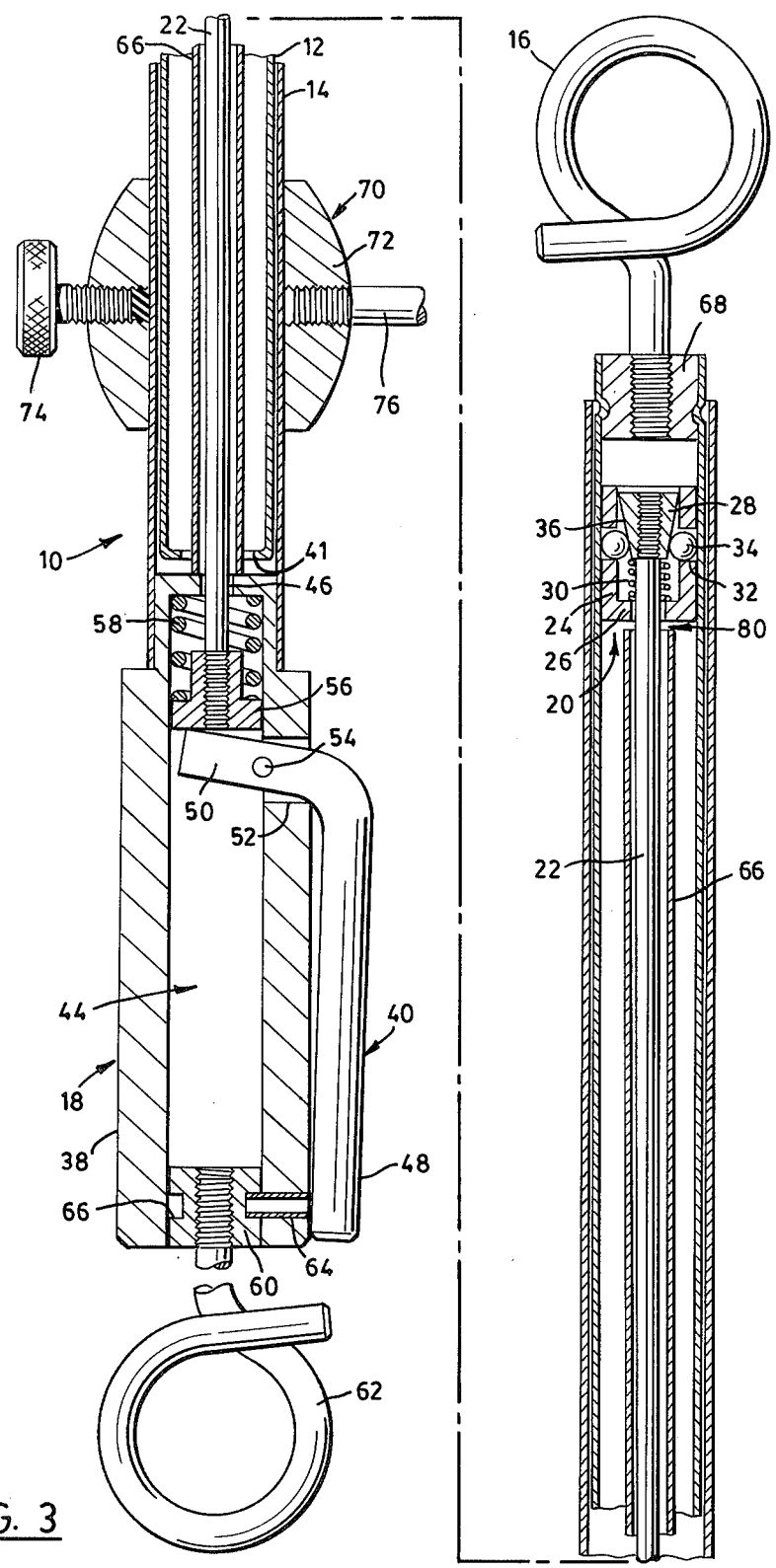
FIG. 3 is a cross-sectional view similar to FIG. 2, showing the suspension support unit activated by pressing the release lever.

The lower end of outer sleeve 14 carries grip 18 which comprises a hollow handle 38 and a lever 40. Outer sleeve 14 is fastened to a hollow boss 42 on the upper end of handle 38 and the lower end of inner cylinder 12, having an inturned lip 41, rests against boss 42 when the sleeve and the cylinder are telescoped together as seen in FIGS. 2 and 3, the inner cylinder having an inturned lip 41 at its lower end. Hollow handle 38 and boss 42 form a cylindrical chamber 44 into which the lower end portion of shaft 22 projects through an aperture 46 in the end of the boss in which the shaft is freely slidable. Lever 40 is angled to form a downwardly projecting gripping arm 48 and a shorter arm 50 projecting into chamber 44 of handle 38 through a radial aperture 52 in the handle, arm 50 being pivotably mounted on the handle by a transverse pin 54 in the area of the radial aperture. The lower end of shaft 22 is threaded to carry a cap 56 which bears laterally against arm 50 of lever 40 and the cap is urged against the arm by a compression spring 58. The bottom end of chamber 44 of handle 38 is closed by a plug 60 which preferably carries a downwardly projecting eye hook 62. Plug 60 is held in handle 38 by a pin 64 engaging a circumferential groove 65 in the plug.

A spacer tube 66 concentric with shaft 22 spaces collar 24 of brake mechanism 20 from boss 42 of handle 38, the collar resting against the upper end of the tube and the lower end of the tube resting against the boss.

The upper end of inner cylinder is closed by a crimped plug 68 into which eye hook 16 is threaded.

Means to support an object is carried by outer sleeve 14, in the form of a hanger 70 in the example embodiment. Hanger 70 comprises a collar 72 slidably mounted on outer sleeve 14 and releasably secured on the sleeve by a screw clamp 74. Collar 72 carries a plurality of fixed, outwardly projecting arms 76 each terminating at its free end in a hook 78.

In the operation of the example embodiment, cylinder 12 and sleeve 14 are locked together when lever 40 is in its released position as seen in FIG. 2 of the drawings. In this position of rest any weight suspended from hook 62 or 78, or even the weight of outer sleeve 14 and grip 18 and shaft 22 if no weight is suspended from the unit, pulls shaft 22 downwardly which causes sides 36 of plug 28 to bear laterally against bearings 34 and to force the bearings against inner cylinder 12. Since inner cylinder 12 and outer sleeve 14 are interconnected through grip 18, the friction of bearings 34 jammed against inner cylinder 12 will prevent their movement relative one to the other. The downward force of plug 28 acts to intensify the wedging action on bearings 34 which, as seen in FIG. 3, are urged in a clockwise rotation.

Figure 4:
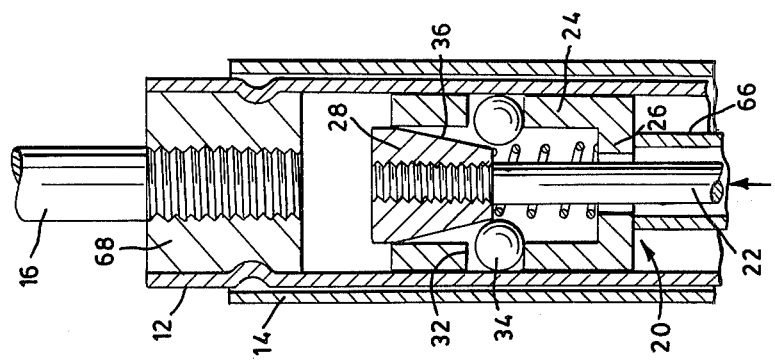
FIG. 4 is a vertical cross-sectional view of the upper end portion of the unit, as in FIGS. 2 and 3, showing the position of the locking mechanism when the handle of the unit is pushed upward.

To lower or raise hanger 70 and eye hook 62, grip 18 is grasped by an operator to depress lever 40, i.e. to move arm 48 of the lever towards handle 38. This pivots lever 40 about pin 54 and causes arm 50 of the lever to bear against cap 56 on shaft 22 as shown in FIG. 3 of the drawings. However, the weight suspended from hook 62 or 78, or even the weight of the handle if no weights are suspended from the unit, keeps bearings 34 jammed against inner cylinder 12 as mentioned above. Therefore the depression of lever 40 moves handle 38 downwardly together with tube 66, creating a gap 80 between flange 26 of braking mechanism 20 and the upper end of the tube. To release braking mechanism 22 for vertical (telescopic) adjustment of unit 10 it is further necessary to move handle 68 upwardly. This upward movement closes gap 80 and causes tube 66 to bear against flange 26 of collar 24. The upward movement of collar 24 causes bearings 34 to be urged in counter-clockwise rotation which releases braking mechanism 20 as seen in FIG. 4 whereupon unit 10 may be vertically adjusted to suit the operator. When the vertical adjustment has been made, unit 10 is locked in the newly selected position by releasing lever 40 whereupon spring 58 draws down plug 28 against bearings 34 and the suspended weight and/or the weight of the unit maintains that relationship, as outlined above with respect to the position of rest of the unit.

It will be appreciated that unit 10 may be rotated on the axis of shaft 22 at the same time that lever 40 is depressed and upward force is applied to grip 18, or when lever 40 is at rest.

I claim:

1. An adjustable suspension support comprising:
   a vertical cylinder and means at the upper end of the cylinder for suspension thereof;
   a shaft coaxially located in the cylinder;
   brake means slidable in the cylinder and comprising a cylindrical collar coaxial with the shaft, the collar having a plurality of radial apertures located in a circumferential plane thereof, the upper end of the shaft carrying a plug located within the collar adjacent the apertures, the plug having an inverted frustro-conical side wall, a plurality of spherical bearings one located in each aperture of the collar and retained therein by the plug to bear laterally against the cylinder;
   grip means carried by the lower end of the shaft and including lever means operable to move the grip means axially downward with respect to the shaft;
   a spacer tube concentric with the shaft and freely slidable thereon, the lower end of the tube abutting the grip means and the upper end abutting the collar when the lever means is not operated; and
   means connected with the support to carry an object;
   whereby on operating the lever means and exerting an upward force on the grip means the plug is raised with respect to the collar and the brake means is thereby released.

2. A support as claimed in claim 1 including an outer sleeve concentric with the cylinder and freely slidable thereon, the sleeve being fixed at the lower end thereof to the grip means.

3. A support as claimed in claim 2 including means projecting outwardly from the sleeve to support an object.

4. A support as claimed in claim 3 in which the outwardly projecting means is slidable along the sleeve and releasably clamped thereon.

5. A support as claimed in claim 3 in which the outwardly projecting means comprises a hanger having a collar slidable on the outer sleeve, and at least one arm projecting outwardly from the collar; said clamping means clamping the collar releasably on the sleeve.

6. A support as claimed in claim 1 in which the grip means comprises a hollow handle defining an inner chamber, the lower end of the shaft projecting into the chamber, the lever means comprising a lever pivoted on the handle intermediate its ends, one end of the lever projecting into the chamber and bearing laterally against the lower end of the shaft.

7. A support as claimed in claim 6 in which the lower end of the shaft is urged against the lever by a compression spring.

8. A support as claimed in claim 1 in which the lower end of the cylinder terminates in an inturned lip whereby the brake means is stopped from passing out therefrom.

9. A support as claimed in claim 1 in which the collar of the brake means includes an inturned flange at the lower end thereof, the upper end of the spacer tube bearing against the flange, and a compression spring within the collar coaxial with the shaft, one end of the spring abutting the flange and the other end of the spring abutting the plug.

10. A support as claimed in claim 1 in which the plug is threaded onto the upper end of the shaft.

* * * * *